United States Patent
Hites et al.

[11] Patent Number: 5,964,592
[45] Date of Patent: *Oct. 12, 1999

[54] NONMETALLIC DENTAL POST AND METHOD

[76] Inventors: Andras A. Hites; George Hites, both of 6665 Amador Plaza Rd., Dublin, Calif. 94568; Chris Pescatore, 525 Park Ave., Plainfield, N.J. 07060

[*] Notice: This patent issued on a continued prosecution application filed under 37 CFR 1.53(d), and is subject to the twenty year patent term provisions of 35 U.S.C. 154(a)(2).

[21] Appl. No.: 08/897,431

[22] Filed: Jul. 21, 1997

[51] Int. Cl.$^6$ .................................................. A61C 5/08
[52] U.S. Cl. .................................... 433/221; 433/224
[58] Field of Search ................................ 433/220, 221, 433/224

[56] References Cited

U.S. PATENT DOCUMENTS

| | | | |
|---|---|---|---|
| 4,396,377 | 8/1983 | Roemer et al. | 433/199 |
| 4,744,753 | 5/1988 | Ross | 433/173 |
| 4,936,776 | 6/1990 | Kwiatkowski | 433/220 |
| 5,035,620 | 7/1991 | Roane | 433/221 |
| 5,085,811 | 2/1992 | Hamer | 264/16 |
| 5,089,183 | 2/1992 | Johnson | 264/16 |
| 5,236,361 | 8/1993 | Mays | 433/221 |
| 5,284,443 | 2/1994 | Weil | 433/224 |
| 5,302,129 | 4/1994 | Heath et al. | 433/224 |
| 5,326,263 | 7/1994 | Weissman | 433/220 |
| 5,328,372 | 7/1994 | Reynaud et al. | 433/221 |
| 5,348,476 | 9/1994 | Cohen et al. | 433/221 |
| 5,487,664 | 1/1996 | Weissman | 433/221 |
| 5,558,517 | 9/1996 | Shalaby et al. | 433/201.1 |
| 5,564,929 | 10/1996 | Alpert | 433/220 |

*Primary Examiner*—John J. Wilson
*Attorney, Agent, or Firm*—Bielen, Peterson & Lampe

[57] ABSTRACT

A dental prosthetic device and method of making and installing the device, the device being a nonmetallic dental post for tooth restoration, the post being fabricated in a mold from a fiber reinforced, ceramic polymer composite, the post having an anchor portion installed in a drilled and reamed post hole with an adhesive and a mounting head portion that is built up with a core material for bonding to a restoration, the post restorative having structural and composition characteristics similar to a natural tooth.

22 Claims, 2 Drawing Sheets

NONMETALLIC DENTAL POST AND METHOD

BACKGROUND OF THE INVENTION

This invention relates to a dental prosthetic device and in particular to a nonmetallic dental post and method of fabrication and installation. The nonmetallic dental post utilizes materials that have found acceptance in dentistry for use in fabricating crowns, bridges and other restorations. Such materials include ceramic optimized polymers and fiber-reinforced composite materials that are tooth-colored and mutually compatible for forming complex restorative structures that are natural in appearances.

In the past, metal in the form of a silver amalgam has been extensively used to fill cavities as a result of treating caries by drilling. In part because of concern for the use of toxic mercury in the amalgam, weakening of the tooth, and in part of aesthetic reasons. New compositions were created to provide a tooth filling that was durable and tooth-like in appearance. Similarly, metal, particularly gold, has been used to fabricate crowns for damaged or endodontically treated teeth. New porcelain and ceramic compositions permit strong cap or crown structures to be fabricated for mounting to the remaining stub of a prepared tooth. However, where insufficient natural tooth remains in order to secure a crown, a structural post is installed in the tooth to provide a mount for the fabricated restorative denture, crowns or bridges.

There are three basic types of posts used in dentistry today: the prefabricated, the cast, and the one piece post and crown. To restore an endodontically treated tooth, conventional dental therapy dictates the placement of a metal post and core, and a metal or porcelain-fused to metal crown that is placed onto the post. Clinically, over time a cemented metallic post often causes a tooth to fracture, sometimes resulting in the loss or extraction of the tooth. To avoid the structural incompatibility of a metal post with a tooth that has had a root canal treatment, the flexible, nonmetallic post of this invention was devised. The nonmetallic post is structurally flexible to distribute forces uniformly in the remaining tooth stub, substantially reducing the potential of fracture. Additionally, the tooth-like color and compatibility of the material forming the nonmetallic post with the natural tooth make the resulting restoration aesthetically pleasing as well as structurally sound.

SUMMARY OF THE INVENTION

The nonmetallic dental post and method of fabrication and installation of the post were devised to enable a dental post to be prefabricated, utilizing materials that have structural and compositional compatibility with the natural tooth being restored. Using a fiber reinforced composite material to fabricate the post and compatible ceramic or polymer composite filler materials for preparing the tooth to receive the post, a structure is formed that provides a flexible, high-strength mount for a crown, bridge or other restoration. The composite post structure has a high flexural strength of 1000 MPa, and is easily and more strongly bonded to composite material crowns and bridges including a preferred ceramic optimized polymer composition used to construct durable, natural looking restorations. The nonmetallic post is tooth-colored, allowing translucent ceramic, porcelain and polymer glass restorations to be mounted and bonded to the post for a natural appearance.

Among the advantages of the nonmetallic post are:

A restoration mount that is tooth colored;

A seating procedure that is light, dual or self curing according to the preference of the dentist;

A higher bond strength due to the similar chemical composition of the post and hybrid resin cement;

A higher bond strength of the core material buildup due to similar chemical composition;

Metal-free which does not break down cement seal over time and does not effect periodontal condition of tooth;

Resiliency—eliminates fracture potential commonly seen with traditional metal posts;

High flexural strength of 1000 megapascals (MPa);

Biocompatible;

Ability to customize for each tooth;

Added retention due to spiral design without introducing weak areas to the fiber reinforced, composite post;

Eliminates extra procedural step of blocking out a dark color of a metal post;

Does not discolor teeth or gingival tissue;

Homogenous restoring of tooth to its original strength;

Fewer sizes (only two) of prefabricated FRC post eliminates large inventory for dentist; and, More economical for dentist because there is no lab fee for indirect fabrication of FRC post.

These and other features of this invention are described in detail in the detailed description of the preferred embodiment.

BRIEF DESCRIPTION OF THE DRAWINGS

FIG. 3 A cross-section of the tooth stub of FIG. 1 with the nonmetallic post being tried in.

DETAILED DESCRIPTION OF THE PREFERRED EMBODIMENTS

The nonmetallic dental post of this invention is designed as a dental prosthetic device that is natural in appearance and used to construct a tooth restoration having structural and biological characteristics similar to the original tooth. The primary advantage of using a non-metal dental post is to construct a restoration that is not only natural in appearance but restores the damaged tooth to an integral structure that is nearly as strong as the original tooth. The use of a metal post for a tooth restoration introduces a material that is not compatible with the original tooth structure or modern composite materials that are preferred for natural appearing restorations. The metal post often causes the remaining natural tooth structure to fracture, resulting in potential loss of the tooth.

Preferably, the nonmetallic post is fabricated using a fiber-reinforced composite material that is composed of layers of fiber wafers as well as uniaxially oriented fiber bundles in a ceramic polymer matrix to provide strength as well as flexibility to the post. The preferred material is a composite material, Vectris™ available from Ivoclar North America, Inc., a division of Ivoclar Williams. The composite material Vectris, has a composition comprising glass fibers (65%), bisphenol A-glycidylmethacrylate (BIS-GMA) (24.5%), decandiol dimethacrylate (0.3%), triethyleneglycol dimethacrylate (6.2%), urethane dimethacrylate (0.1%), highly dispersed silica (3.5%) catylists and stabilizers (<0.3%) and pigments (<0.1%) This material has in the past been utilized for dental frameworks in the construction of bridges, clasps and other dental restorative support structures. The material is favored for its natural tooth-like coloring and compatibility with composites used in forming restorations and the adhesives used in bonding the restorations to the frameworks. The high strength, light-weight material is flexible, allowing forces applied to a nonmetallic post created of such material to be evenly distributed to the remaining tooth in which the post is anchored.

The nonmetallic post is preferably prefabricated in quantities of 1 or 2 standard sizes. In this manner, a dentist can utilize the compatible sized drills and reamers to construct a post hole for the standard sized posts. Custom fabrication of a post with the required additional visit by the patient is thereby avoided.

Figure 1:
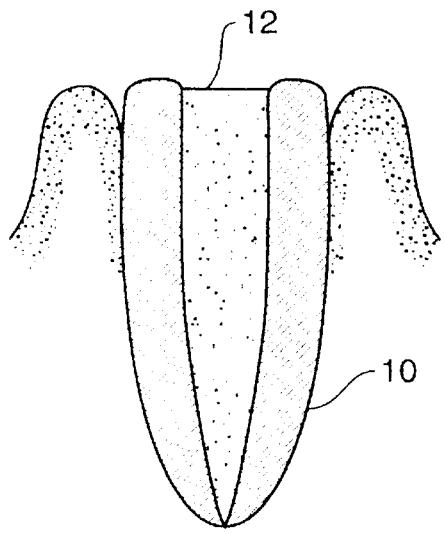
FIG. 1 A cross-section of an endodontically prepared tooth stub.

The nonmetallic post is preferably formed in a mold. For example, the nonmetallic post may be formed by the construction of a mold from a post prototype to create a mold cavity in a conventional manner. The fiber-reinforced composite material and the ceramic optimized polymer material are packed and pressed into the mold cavity and cured using light, heat pressure and vacuum. After curing (polymerization) the post is removed from the mold. Further curing is then carried out under light and heat. The finished product is shown in FIG. 1.

The mold may be constructed in any other traditional manner. Preferably, the mold is light transmissible to take advantage of post materials used in fabricating the post that are polymerized using light. Additionally, a light transmitting rod can be added or made part of the nonmetallic post to improve the transmission of light and to enhance the curing of the resin. Although this is particularly helpful on a long root canal, when using dual cure bonding resins it is not necessary.

Referring to the drawings, a typical configuration for the nonmetallic dental post is shown with a recommended procedure for constructing a typical restoration. In FIG. 1, a tooth stub 10, here the root of a broken cuspid, for example, has been endodontically treated with a root canal filling material 12 such as gutta percha.

Figure 2:
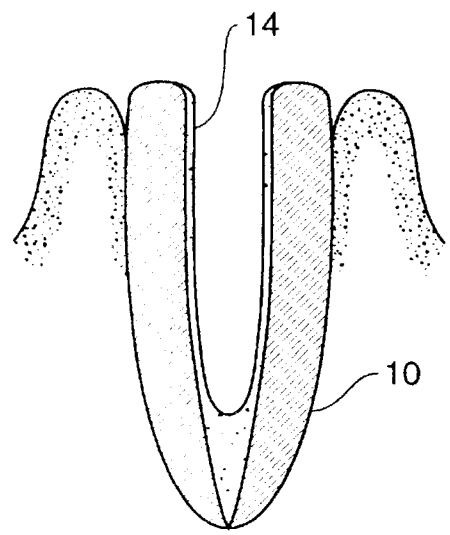
FIG. 2 A cross-section of the tooth stub of FIG. 1 prepared with a reamer.

In FIG. 2, the appropriate amount of root canal filling material is removed by drilling and the resulting hole or canal 14 is shaped with the correct size reamer for the post to be inserted.

Figure 3:
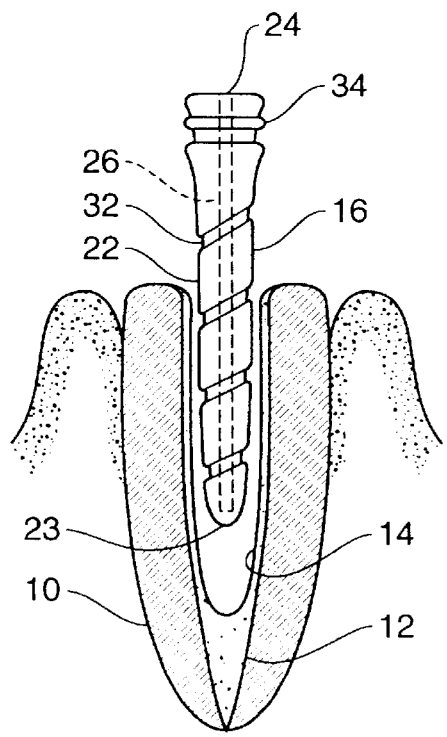

In FIG. 3, the nonmetallic post 16 of appropriate size is then tried in the canal to verify fit. At this time any customizing of the post can be done.

Figure 4:
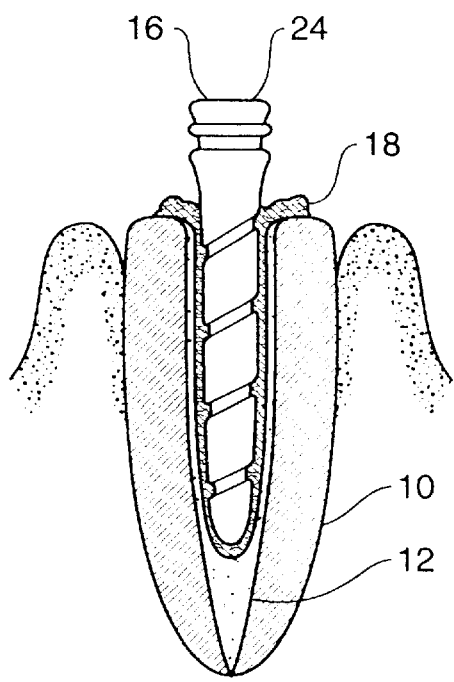
FIG. 4 A cross-section of the tooth stub of FIG. 1 with a the nonmetallic post inserted into the canal with resin cement.

Referring to FIG. 4, the post hole or canal 14 is treated using state-of-the-art adhesive dental protocol. The post is microetched and cleaned. Silane agent is then applied to the post, dried, and a dual-cure adhesive is brushed on. A resin cement 18 such as Variolink, or Variolink II (Vivadent) is then injected into the canal and the post is inserted and seated. The resin cements, Variolink and Variolink II are fiberless methacrylate compositions as defined for Vectris that are 74% filled by weight with ground glass and silica dioxide of an average particular size of 0.7 microns. They come in multiple shades, three viscosities, continuous fluoride release, and are both light and dual curing. Light-curing is then performed to initiate the setting of the resin cement.

The preferred polymer materials for forming the post are light transmissible allowing the effective use of light in curing the resin cements used in bonding the post to the tooth and placing the restoration 28 on the post and core. Additionally, as noted a light transmissible rod 26 shown in dotted line in FIG. 3, may be included during fabrication of the post 16 to improve curing using light as mentioned.

Figure 5:
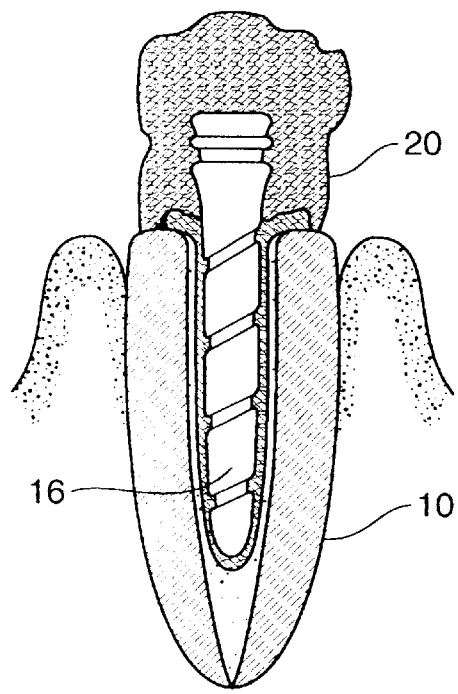
FIG. 5 A cross-section of the tooth stub of FIG. 1 with the nonmetallic post bonded in place and the core material added to the remainder of the post.

In FIG. 5, a hybrid resin such as Tetric (Ivoclar Williams) is added to the projecting mounting portion or head 24 of the post and light-cured. This will serve as the core 20 to which the restoration will be attached.

Figure 6:
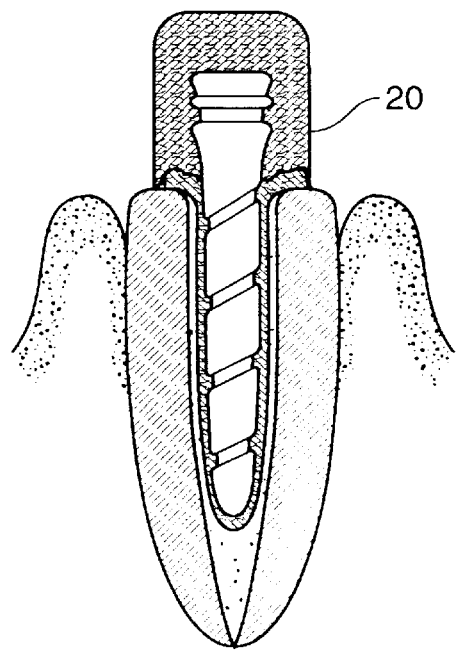
FIG. 6 A cross-section of the final (crown) preparation of the restored tooth stub of FIG. 1.
Figure 7:
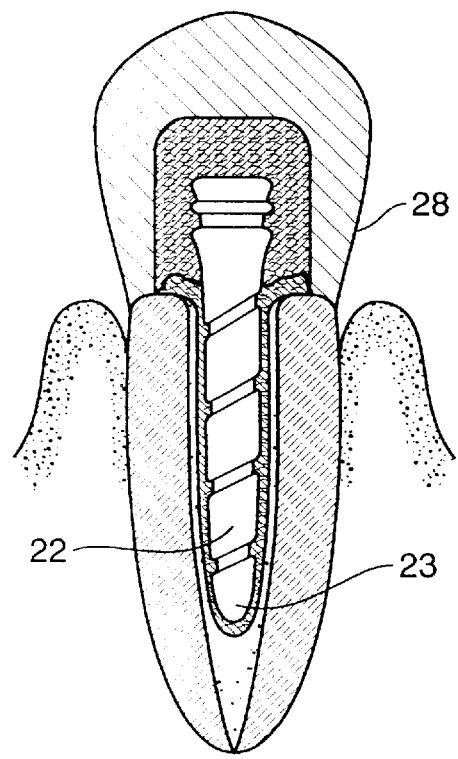
FIG. 7 A cross-section of the final restoration, in the form of a crown, over the restored tooth stub.

In FIG. 6 and 7, the core is shaped and the finished preparation is then accomplished. The desired restoration 28 (a crown in this case) is then placed on the post and core using modern bonding techniques.

The nonmetallic post 16, as shown in FIGS. 3 to 7, is constructed with an elongated cylindrical anchor portion 22 with a tapered end 23 that preferably has a spiral groove 32 which assists in uniform distribution of the adhesive cement used in bonding the post to the tooth stub. Additionally, the mounting portion or head 24 of the post 18 has grooves which improve the bonding of the restoration 28 to the post 18.

Dimensionally, the post has a length of approximately 12 millimeters and a diameter at its mount portion 34 of approximately 2 millimeters. As noted, a limited number of standard sizes is preferred to enable the post to be selected from one of a limited number of sizes and installed using tools that are limited in number and that are compatible with the post sizes. Additionally, it is to be understood that other configurations of the post structure can be fabricated, for example a post with a conical anchor portion and a rectangular mount portion. Grooves in the anchor portion and mount portion of the nonmetallic post can be eliminated where suitable bonding materials are employed.

The Targis-Vectris materials are preferred for use in the tooth reconstructions. The Targis ceramic optimized polymer is preferred to restore the core of an endodontically-treated tooth to its original strength without introducing the possible detrimental affects of metal and to improve the adhesion of the compatible Targis-Vectris fabricated post to the reconstructed core. A Targis, ceramic optimized polymer is preferred for the restoration again for compositional compatibility with the preferred nonmetallic material of the post and core. The Targis ceramic optimized polymer is a 72% silanized barium glass filler is a matrix of 9% urethane, dimethacrylate, 4.6% decandiol dimethacrylate, 8.7 bis-GMA, 5% highly dispersed silica, 0.6% catalyst and stabilizer and 2% or less in pigments.

It is to be understood that alternate methods may be utilized in preparing a tooth for installation of the nonmetallic post of this invention. For example, the post hole may be formed utilizing a mandril with a composite fill material that is cured or partially cured prior to removal of the mandril, which is sized to conform to the anchor portion of the pre-fabricated post. Additionally, the nonmetallic post can be used to anchor a bridge or framework for a multi-tooth restoration.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental post for use in mounting a permanent tooth restoration comprising:

an elongated post member fabricated of a nonmetallic composition having an anchor portion adapted to seat in a prepared tooth canal and a mounting portion adapted to construct a tooth core for mounting a permanent tooth restoration on the installed post wherein the post-member is prefabricated in a mold from a fiber-reinforced composite material having a strength and flexibility approximating natural tooth material, wherein the elongated post member is fabricated from a polymer composite material forming a unitary, flexible mounting structure having a flexible strength of approximately 1000 megapascals and is fabricated in a mold from a fiber-reinforced composite material having a glass fibers in a methacrylate polymer matrix.

2. The dental post of claim 1 wherein the elongated post member is fabricated in a mold from a curable ceramic-polymer and fiber composite that is packed in the mold and cured.

3. The dental post of claim 1 wherein the elongated post member is fabricated in a mold, wherein the mold is constructed with a cavity formed by a prototype post member, wherein the mold comprises a polysiloxane impression material that is cured, the cavity being formed by removal of the prototype post member.

4. The dental post of claim 1 wherein the anchor portion has a spiral groove.

5. The dental post of claim 1 wherein the mounting portion has at least one circumferential groove.

6. The dental post of claim 1 wherein the post member is tooth colored.

7. The dental post of claim 1 wherein the post member is fabricated from a material having a bio-compatibility with a natural tooth.

8. The dental post of claim 1 wherein the post member is fabricated from a material having a structural compatibility with a natural tooth.

9. The dental post of claim 1 wherein the post member is prefabricated in a limited number of post sizes.

10. The dental post of claim 1 wherein the post member is fabricated from a material having a chemical composition compatible with a polymer ceramic core material.

11. The dental post of claim 1 wherein the post member is fabricated from a light transmissible material.

12. The dental post of claim 1 wherein the fiber-reinforced composite is comprised of layers of fiber wafers and uniaxially oriented fiber bundles in a methacrylate polymer matrix that is ceramic optimized.

13. A method of dental restoration of a tooth using a nonmetallic post having an anchor portion and a head portion comprising the steps of:

a.) structurally preparing the tooth for drilling a post hole;

b.) selection one of a plurality of prefabricated nonmetallic posts having a fiber-reinforced composite material having a strength and flexibility approximating natural tooth material wherein the elongated post member is fabricated from a polymer composite material forming a unitary, flexible mounting structure having a flexible strength of approximately 1000 megapascals and is fabricated in a mold from a fiber-reinforced composite material having glass fibers in a methacrylate polymer matrix;

c.) drilling a post hole conforming to the anchor portion of the selected nonmetallic post;

d.) injecting a resin adhesive into the post hole;

e.) coating the anchor portion of the nonmetallic post with an adhesive;

f.) installing the post in the hole;

g.) building a restoration core on the head of the post;

h.) shaping the restoration core to receive a restoration; and, i.) adhering a restoration to the core and head of the post.

14. The method of claim 13 wherein the step of drilling a post hole includes a step of reaming the post hole.

15. The method of claim 13 wherein the step of coating the anchor portion of the nonmetallic post includes a preliminary step of etching the anchor portion of the post.

16. The method of claim 13 wherein the step of coating the anchor portion of the nonmetallic post is preceded by the step of placing the post in the hole to check the fit.

17. The method of claim 13 wherein the nonmetallic post is fabricated of a light transmissible material and after installing the post in the hole the added step of curing the resin adhesive with light is performed.

18. The method of claim 17 wherein the step of adhering a restoration to the core and head of the post uses a resin adhesive.

19. The method of claim 18 with the added steps of curing the resin adhesive with light after adhering a restoration to the core and head of the post.

20. A method of dental restoration of a tooth using a nonmetallic post having an anchor portion and a head portion comprising the steps of:

a. providing a plurality of elongated prefabricated post members fabricated from a polymer composite material forming a unitary, flexible mounting structure having a flexible strength of approximately 1000 megapascals and is fabricated in a mold from a fiber-reinforced composite material having glass fibers in a methacrylate polymer matrix;

b. structurally preparing the tooth for drilling a post hole;

c. selecting one of the elongated prefabricated posts;

d. drilling a post hole conforming to the anchor portion of the nonmetallic post;

e. injecting a resin adhesive into the post hole;

f. coating the anchor portion of the nonmetallic post with an adhesive;

g. installing the post in the hole;

h. building a restoration core on the head of the post;

i. shaping the restoration core to receive a restoration; and, j. adhering a restoration to the core and head of the post; wherein the step of coating the anchor portion of the nonmetallic post includes a preliminary step of etching the anchor portion of the post.

21. The method of claim 20 wherein the step of coating the anchor portion of the nonmetallic post is preceded by the step of placing the post in the hole to check the fit.

22. The method of claim 20 wherein the step of adhering a restoration to the core and head of the post uses a resin adhesive.

* * * * *